United States Patent [19]

Gaunaurd et al.

[11] 4,249,421
[45] Feb. 10, 1981

[54] METHOD TO DETERMINE THE SHEAR ABSORPTION OF A RUBBERLIKE MATERIAL

[75] Inventors: Guillermo C. Gaunaurd, Rockville; Herbert M. Überall, Bethesda; Kurt P. Scharnhorst, Columbia, all of Md.

[73] Assignee: The United States of America as represented by the Secretary of the Navy, Washington, D.C.

[21] Appl. No.: 87,269

[22] Filed: Oct. 22, 1979

[51] Int. Cl.³ ............................................. G01N 29/00
[52] U.S. Cl. ....................................... 73/589; 73/602; 73/659
[58] Field of Search ................. 73/579, 589, 596, 597, 73/599, 602, 658, 659

[56] References Cited

U.S. PATENT DOCUMENTS

| | | | |
|---|---|---|---|
| 3,315,520 | 4/1967 | Carnevale et al. | 73/597 |
| 3,630,307 | 12/1971 | Kamps | 73/599 |
| 3,824,842 | 7/1974 | Wirt et al. | 73/599 |
| 3,861,200 | 1/1975 | Dory | 73/602 |
| 3,960,004 | 6/1976 | Wirt et al. | 73/599 |
| 4,004,456 | 1/1977 | Vahaviolos | 73/658 |

OTHER PUBLICATIONS

E. Meyer et al.; "Pulsation Oscillations of Cavities in Rubber", *Journal of the Acoustical Society of America*, vol. 30, No. 12, pp. 1116–1124, Dec. 1958.

G. Gaunaurd et al.; "New Method to Determine Shear Absorption using Visco Elasto Dynamic Resonance-Scattering Formalish,"*Journal of Acoustical Society of America*, vol. 64, No. 4, pp. 1211–1212, Oct. 1978.

G. Gaunburd et al., "Giant Monopole Resonances in Scattering Waves from Gas Filled Cavities and Bubbles," *J. Acoust. Soc. Am.*, vol. 65, No. 3, pp. 573–594, Mar. 1979.

*Primary Examiner*—Stephen A. Kreitman
*Attorney, Agent, or Firm*—R. S. Sciascia; A. L. Branning; D. A. Lashmit

[57] ABSTRACT

The shear absorption of a viscoelastic material is determined by directing acoustical energy at the viscoelastic material and sampling the backscattered signals that result when compressional waves propagate through the material and are scattered by either a fluid-filled or evacuated cavity contained therein. The backscattered signals are converted to a resonance amplitude versus frequency domain and the shear absorption of the viscoelastic material is determined from the frequency and the half-width of the resonance peaks.

4 Claims, 2 Drawing Figures

METHOD TO DETERMINE THE SHEAR ABSORPTION OF A RUBBERLIKE MATERIAL

BACKGROUND OF THE INVENTION

This invention relates generally to a method of accurately determining the characteristics and properties of materials, and more particularly to a method for determining the shear absorption parameter in viscoelastic materials.

In many acoustical applications it is necessary to know the shear absorption of a particular composition or sample of a viscoelastic material, for example, to determine whether the material will be an effective sound absorber. Or, it may be necessary to determine the effect of a change in composition on the absorption effectiveness of the material. However, while this is one of the most important viscoelastic parameters, it is also one of the most difficult to determine.

Conventional methods of determining shear absorption do not involve a measurement of acoustical parameters that can be directly correlated with the shear absorption, rather, the desired parameter is derived by subtracting the effects of various other parameters from the overall acoustic response of the material under consideration. This method is less than accurate and is quite cumbersome. One particular method requires that a shear wave be made to longitudinally propagate along a strip of the material while measurements are made of the amplitude decay of the wave as it travels along the strip. This may require various strip thicknesses, and in general such methods are laborious.

SUMMARY OF THE INVENTION

Accordingly, the present invention overcomes many of the above difficulties by providing a more accurate and direct method for determining the shear absorption of a viscoelastic material.

In one embodiment, acoustical energy is directed at a sample of viscoelastic material having therein a fluid-filled or evacuated cavity. Measurements are taken of the compressional waves that propagate through the material and are backscattered from the cavity. From the amplitude versus frequency response of the backscattered waves, the half-widths of the resonance peaks are plotted against the resonance frequencies, from which the shear absorption parameter of the material is calculated.

OBJECTS OF THE INVENTION

It is therefore an object of the present invention to provide an accurate and more direct method for determining the shear absorption parameter of a viscoelastic material.

Another object of the present invention is to provide a less complex method for determining shear absorption using conventional acoustic apparatus.

Still another object of the present invention is to provide a method for correlating the shear absorption of a material with the resonance half-width and the resonance frequency of a fluid-filled or an evacuated cavity within a viscoelastic material.

BRIEF DESCRIPTION OF THE DRAWING

Other objects and many of the attendant advantages of this invention will be readily appreciated as the same becomes better understood by reference to the following detailed description when considered in connection with the accompanying drawing, in which like reference numerals designate like parts and wherein.

DESCRIPTION OF THE PREFERRED EMBODIMENT

Figure 1:
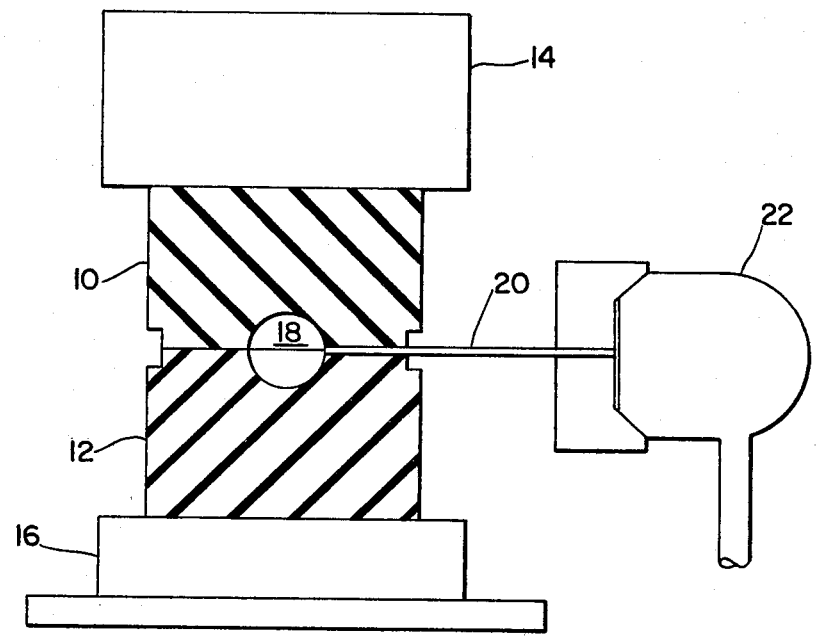
FIG. 1 is a partial cross-sectional view of test apparatus for obtaining the resonance response of a viscoelastic material.

Referring now to the drawing, there is shown in FIG. 1 conventional test apparatus for measuring the resonance response of a cavity within a sample of viscoelastic material. A pair of rectangular blocks 10, 12 formed of a viscoelastic material, such as rubber, are held in place between a weight 14 and a piezoelectric acoustic transducer 16. A semispherical depression is molded into each block 10, 12 at the interface thereof, so that when the blocks are mounted in the test apparatus a spherical cavity 18 is formed approximately midway between transducer 16 and weight 14. An additional depression in each block forms a cylindrical channel leading from cavity 18 to one edge of the blocks. An acoustic probe 20 is inserted into the cylindrical channel so that one end is flush with the surface of cavity 18, the other end of probe 20 being coupled to a condenser microphone 22. Probe 20 may conveniently be filled with a dampening material so that the dynamic range of microphone 22 will not be exceeded by the amplitude of the acoustical signals generated by transducer 16. Prior to taking any data measurements microphone 22 is calibrated in any conventional manner, for example, by the pressure chamber reciprocity method.

In operation, tranducer 16 generates acoustic signals that cause compressional or p-waves to propagate through blocks 10 and 12. Backscattered waves or pulsation oscillations of cavity 18 are detected by probe 20. The acoustic signals are coupled by probe 20 to microphone 22 where they are converted into electrical signals, from which a spectral resonance response may be obtained in any conventional manner such as a chart recorder or oscilloscope.

It has been shown that a cavity in a solid can exhibit pulsation oscillations and that the cavity has a natural pulsation oscillation or resonance. In the viscoelastic scattering of compressional waves from cavities in lossy materials, a prominent role is played by the monopole or "breathing-mode" resonance of the cavity. In the present method it has been determined that the monopole circular resonance frequency, $\omega_o$, contains two contributions, $\omega_{os}$ and $\omega_{of}$, such that $$\omega_o^2 = \omega_{os}^2 + \omega_{of}^2 \qquad (1)$$

where $\omega_{os}$ is the fundamental shear-wave resonance frequency of evacuated cavities and $\omega_{of}$ is a correction to this frequency caused by the resonance vibrations of a filler medium in the cavity. The quantities $\omega_{os}$ and $\omega_{of}$ may be further defined by $$\omega_{os} = 2c_s/a$$

$$\omega_{of} = (3\rho_f c_f^2/\rho a^2)^{\frac{1}{2}}$$

where $c_s$ is the shear speed of the medium surrounding the cavity, $\rho_f$ and $c_f$ are the density and sound speed of the filler-medium, $\rho$ is the density of the cavity wall material, and a is the cavity radius. Also, the dimensionless wave number of dilatational (compressional) waves in the cavity wall at the resonance frequency, $x_o$, can be expressed as $$x_o = k_{do}a = \omega_o(a/c_d)$$

where $c_d$ is the speed of the dilatational waves.

The normalized non-mode converted scattering amplitude, $f_o{}^{pp}$, in the monopole case can be expressed near the resonance in what is denoted as the standard on linearized Breit-Wigner resonance form $$\frac{1}{a} f_o^{pp}(\pi) = \frac{-(\omega_o/2)(1 + i2\delta_s)}{\omega - \omega_o' + \frac{i}{2}\Gamma_o} \quad (2)$$

where the resonance frequency $\omega_o'$, which is shifted from $\omega_o$ by wall losses, and the full width at half maximum, $\omega_o$, of the resonance peak are, respectively, $$\omega_o = \omega_o + \delta_{s\,of}x_{of} + \omega_o x_o \delta_d/2 \quad (3a)$$
$$\Gamma_o = \omega_o[x_o + \delta_s(\omega_{os}/\omega_o)^2] \quad (3b)$$

In equations (3a) and (3b):

$$x_o^2 = x_{os}^2 + x_{of}^2, \quad x_{os} = 2\,c_s/c_d, \quad x_{of} = 3\rho_f c_f^2/c_d^2 \quad (4)$$

and the loss parameters of the wall material, $\delta_d$, $\delta_s$, for dilatational and shear waves, respectively, are $$\delta_d = \omega M/2 = (F + 2F_1)/2\rho c_d^2 = \frac{\omega}{2}\left(\frac{\lambda_v + 2\mu_v}{\lambda_e + 2\mu_e}\right) \quad (5a)$$

$$\delta_s = \omega N/2 = F_1/2\rho c_s^2 = \frac{\omega}{2}\left(\frac{\mu_v}{\mu_e}\right). \quad (5b)$$

Here, $\mu_e$ and $\lambda_e$ are the elastic Lame' parameters and $\mu_v$ and $\lambda_v$ are their viscous counterparts, so that $\lambda = \lambda_e = i\omega\lambda_v$ and $\mu = \mu_e - i\omega\mu_v$ are the complex Lame' parameters.

From Equation (3b) the relative half-width, $\Gamma_o/2\omega_o$, of a resonance peak can be expressed as a function of a straight line:

$$\Gamma_o/2\omega_o = m\,f_o + I \quad (6)$$

where the intercept I and the slope m are given by $$I = \frac{c_s}{c_d}\eta^{\frac{1}{2}}\quad m = \pi N/\eta \quad (7)$$

and the parameter $\eta$ is defined by $$\eta = 1 + \frac{3\rho_f c_f^2}{4\rho\,c_s^2}.$$

N is the shear absorption parameter which is sought to be determined.

The weak absorption assumption ($\delta_s<<1$) is used in Equation (3). It is now evident that if the cavity is evacuated ($\rho_f=0$) and if the wall material is non-absorbing (i.e., N=0), then $\eta=1$ and m=0, respectively.

Figure 2:
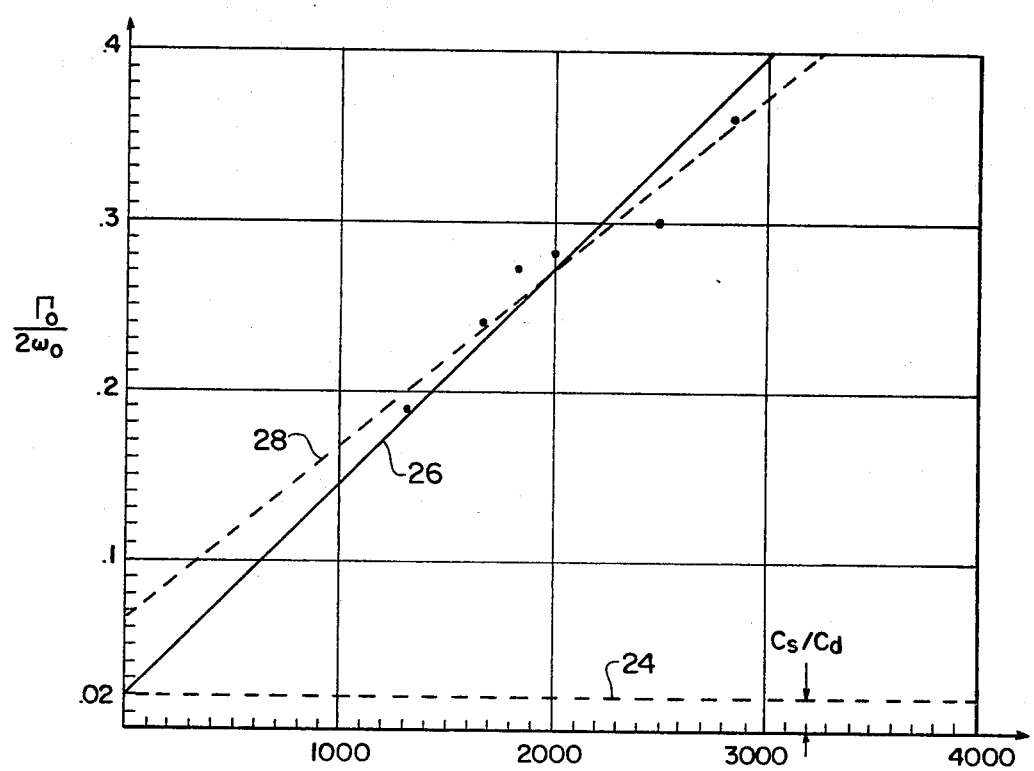
FIG. 2 is a graph of the resonance half-width versus resonance frequency for rubber showing the linear relationship thereof from which the shear absorption is determined.

FIG. 2 is a plot of the normalized resonance half-width versus resonance frequencies of the resulting peaks produced by the viscoelastic scattering of p-waves from air-filled spherical cavities in lossy rubber. The straight line in this case is horizontal with intercept $I = c_s/c_d$, as represented by dashed line 24. This was the result predicted in the prior art, assuming no filler medium in the cavity and no absorption in the cavity wall. It was assumed that the discrepancy between actual data points, shown in FIG. 2, and line 24 were due to absorptive losses in the viscoelastic material.

The present method, however, correlates the resonance peak half-width $\Gamma_o/2\omega_o$ and the resonance frequency $f_o$ so that the shear absorption N can be calculated.

Measurements were taken using the apparatus shown in FIG. 1, where the blocks of viscoelastic material 10, 12 were formed of an "FJ-95" rubber (indicating the DVM hardness) and cavity 18 was filled with air. FJ-95 rubber has the following parameters: $c_d = 1.5\times 10^5$ cm/sec; $c_s = 0.03\times 10^5$ cm/sec; $\rho = 1.13$ g/cm$^3$; and air has the parameters: $\rho = 0.0012$ g/cm$^3$, $c_f = 0.344\times 10^5$ cm/sec. From the spectral response of the rubber, the relative half-widths, $\Gamma_o/2\omega_o$, of the resonance peaks were plotted as a function of the resonance frequency, $f_o$, as represented by the data points in FIG. 2. Dashed line 28 represents the "least square" approximation for the given data points and solid line 26 is the Chebyshev or min-max line, which has a slope m $\approx 1.2\times 10^{-4}$, and an intercept I$\approx 0.02$ that is close to the value of the intercept predicted by prior art methods. Using the above parameters an $\eta$-value of $\eta = 1.105$ and an intercept I=0.022 (from Equation (7)) are obtained.

The slope of min-max line 26 is now used to determine the value of the viscous shear absorption parameter N. From Equation (7)

$$N = m\eta/\pi = 1.105\times 1.2\times 10^{-4}/3.14 \approx 4.22\times 10^{-5}$$
sec.

This result and the relation $\mu_v = N(\rho c_s^2)$ yield $\mu_v \approx 4.3\times 10^2$ dyne-sec/cm$^2$. The value of N can be used to find an upper bound on $f_o$ for the weak absorption assumption, $\delta_s = \omega_o N/2<<1$. If $\delta_s \approx \frac{1}{3}$, then $f_o$ can be as high as 2.7 kHz for the weak absorption assumption still to be valid.

Therefore, using the fact that the relative half-width of the resonance peaks is linearly dependent on the fundamental resonance frequency of the cavity, the spectral response of the scattering amplitude of air-filled cavities in visoelastic materials can be used to determine the shear absorption parameter of the material.

Obviously, many modifications and variations of this invention are possible in the light of the above teachings. It is, therefore, to be understood that within the scope of the appended claims the invention may be practiced otherwise than as specifically described.

What is claimed and desired to be secured by Letters Patent of the United States is:

1. A method for determining the shear absorption of a viscoelastic material comprising the steps of:
   forming a cavity of known dimensions within a sample of said viscoelastic material, wherein said cavity is filled with a fluid having a known density and wavespeed;
   directing incident acoustic waves containing a predetermined frequency spectrum at said viscoelastic material, thereby creating compressional waves in said material that impinge upon said cavity and create therein a set of modal resonances;
   receiving a portion of said waves backscattered from said cavity;
   converting said received waves into electrical signals;

obtaining from said electrical signals a spectral response of said backscattered waves comprising a modulus of resonance amplitudes as a function of frequency, said modulus comprising a plurality of resonance peaks corresponding to the fundamental and overtone resonances of said cavity;

measuring the width of a plurality of said resonance overtones at a point one half-width below the maximum value of each of said overtones;

plotting said resonance overtone half-widths as a function of the corresponding resonance frequency of each of said overtones and fitting a straight line through a locus of points defined by said plot of overtone half-widths; and deriving the slope of said straight line and obtaining therefrom the shear absorption of said viscoelastic material, wherein said shear absorption is proportional to the slope of said line, the density and wavespeed of said viscoelastic material, and the density and wavespeed of said fluid within said cavity.

2. The method of claim 1 wherein said shear absorption, N, is defined by the relation $$N = \frac{m}{\pi} (1 + (\frac{3\rho_f c^2}{4\rho c_s^2}))$$

where m is the slope of said straight line, $\rho_f$ and $c_f$ are the density and wavespeed, respectively, of said cavity filler-fluid, and $\rho$ and $c_s$ are the density and wavespeed, respectively, of said viscoelastic material.

3. The method of claims 1 or 2 wherein said step of receiving a portion of said waves comprises the step of: sampling the sound pressure level variations within said cavity.

4. A method for determining the shear absorption of a viscoelastic material having therein one or more cavities, said cavities being filled with a fluid having a known density and wavespeed, comprising the steps of:

directing incident acoustic waves containing a predetermined frequency spectrum at said viscoelastic material, thereby creating compressional waves in said material that impinge upon said cavity and create therein a set of modal resonances;

receiving a portion of said waves backscattered from said cavity;

converting said received waves into electrical signals;

obtaining from said electrical signals a spectral response of said backscattered waves comprising a modulus of resonance amplitudes as a function of frequency, said modulus comprising a plurality of resonance peaks corresponding to the fundamental and overtone resonances of said cavity;

measuring the width of a plurality of said resonance overtones at a point one half-width below the maximum value of each of said overtones;

plotting said resonance overtone half-widths as a function of the corresponding resonance frequency of each of said overtones and fitting a straight line through a locus of points defined by said plot of overtone half-widths; and deriving the slope of said straight line and obtaining therefrom the shear absorption of said viscoelastic material, wherein said shear absorption is proportional to the slope of said line, the density and wavespeed of said viscoelastic material, and the density and wavespeed of said fluid within said cavity.

* * * * *